(12) United States Patent
Tang et al.

(10) Patent No.: US 8,628,972 B2
(45) Date of Patent: Jan. 14, 2014

(54) MICROFLUIDIC DEVICES AND METHODS FOR MALARIA DETECTION

(75) Inventors: William C. Tang, Irvine, CA (US); Yu-Hsiang Hsu, Pasadena, CA (US)

(73) Assignee: The Regents of the University of California, Oakland, CA (US)

( * ) Notice: Subject to any disclaimer, the term of this patent is extended or adjusted under 35 U.S.C. 154(b) by 38 days.

(21) Appl. No.: 13/347,551

(22) Filed: Jan. 10, 2012

(65) Prior Publication Data

US 2012/0190060 A1      Jul. 26, 2012

Related U.S. Application Data

(60) Provisional application No. 61/431,558, filed on Jan. 11, 2011.

(51) Int. Cl.
*G01N 33/48* (2006.01)
*C12Q 1/04* (2006.01)
*C12Q 1/06* (2006.01)

(52) U.S. Cl.
USPC ............... 436/63; 436/164; 436/180; 435/2; 435/29; 435/34; 435/39; 422/73; 422/502; 422/503

(58) Field of Classification Search
USPC ............ 436/63, 70, 164, 165, 174, 180; 422/68.1, 73, 82.05, 501, 502, 503, 422/504, 505; 435/2, 4, 29, 30, 34, 39, 325, 435/287.3
See application file for complete search history.

(56) References Cited

U.S. PATENT DOCUMENTS

| | | | | |
|---|---|---|---|---|
| 7,833,486 B2* | 11/2010 | Fielden et al. | ............... | 422/502 |
| 2010/0104479 A1* | 4/2010 | Gu et al. | ............... | 422/102 |
| 2011/0124095 A1* | 5/2011 | Manalis et al. | ............ | 435/287.1 |
| 2011/0151479 A1* | 6/2011 | Stevens et al. | ............... | 435/7.1 |
| 2011/0266151 A1* | 11/2011 | Jansson | ......................... | 204/451 |
| 2013/0130226 A1* | 5/2013 | Lim et al. | ......................... | 435/2 |

OTHER PUBLICATIONS

Antia, Meher et al., Microfluidic modeling of cell-cell interactions in malaria pathogenesis, PLOS Pathog., 3(7): 939-948 (2007).
Hung, Paul J. et al., A novel high aspect ratio microfluidic design to provide a stable and uniform microenvironment for cell growth in a high throughput mammalian cell culture array, Lab Chip 5: 44-48 (2005).
Nash, GB, et al., Rheological analysis of the adhesive interactions of red blood cells parasitized by *Plasmodium falciparum*, Blood, 79(3): 798-807 (1992).
Shelby, J. Patrick, et al., A microfluidic model for single-cell capillary obstruction by *Plasmodium falciparum* infected erythrocytes, Proc Natl Acad Sci USA, 100(25): 14618-14622 (2003).

(Continued)

*Primary Examiner* — Maureen Wallenhorst
(74) *Attorney, Agent, or Firm* — Vista IP Law Group LLP

(57) ABSTRACT

A device for identifying infection by the malaria parasite includes a microfluidic device having an inlet and an outlet and a diagnostic channel interposed between the inlet and the outlet. The diagnostic channel includes a contact surface and a sample pump configured to pump a RBC-containing sample into the inlet. The contact surface may be at least one of hydrophilic and roughened. Malaria infected RBCs (miR-BCs) interact with the contact surface and become immobilized thereon whereas non-infected RBCs continue to flow downstream in the diagnostic channel.

13 Claims, 10 Drawing Sheets

(56) References Cited

OTHER PUBLICATIONS

Wongchotigul, Varee et al., The use of flowcytometry as a diagnostic test for malaria parasites, Flow Cytom. Malaria Detection, 35(3): 552-559 (2004).

Zimmerman, Peter A. et al., Diagnosis of Malaria by Magnetic Deposition Microscopy, Am. J. Trop. Med. Hyg., 74(4), 2006, pp. 568-572 (2006).

Lee, Gwo-Bin et al., Micromachine-based multi-channel flow cytometers for cell/particle counting and sorting, J. Micromech, Microeng. 15 (2005) 447-454.

* cited by examiner

MICROFLUIDIC DEVICES AND METHODS FOR MALARIA DETECTION

RELATED APPLICATION

This Application claims priority to U.S. Provisional Patent Application No. 61/431,558 filed on Jan. 11, 2011. Priority is claimed pursuant to 35 U.S.C. §119. The above-noted Patent Application is incorporated by reference as if set forth fully herein.

STATEMENT REGARDING FEDERALLY SPONSORED RESEARCH OR DEVELOPMENT

This invention was made with Government support of Grant No. HR0011-06-1-0050, awarded by the Department of Defense. The Government has certain rights in this invention.

FIELD OF THE INVENTION

The field of the invention generally relates to diagnostic devices and associated methods for detecting infection by the malaria parasite.

BACKGROUND

Malaria is one of the leading causes of death in developing countries, where four strains of malaria parasites have been identified to be infectious to human, which include *Plasmodium falciparum, Plasmodium vivax, Plasmodium ovale*, and *Plasmodium malariae. Plasmodium falciparum* is particularly life threatening due to its high morbidity and mortality rate. Pregnant women, infants, and children with compromised immune functions are most vulnerable to infection. To suppress possible pandemic outbreaks of malaria, substantial research efforts have been devoted to early diagnosis and treatment of malaria (EDTM) as the first-line defense against the progression of malaria. These are designed to minimize the spread in endemic regions, and to prevent the transfer of parasites to other countries through tourism. According to the Center for Disease Control (CDC), the onset of flu-like symptoms begins on the ninth to the fourteenth days after infection, and treatment must be administered within twenty-four hours after the start of symptoms. Delay in diagnosis is the major cause of deaths for most infected travelers. Thus, early diagnosis plays the vital role in the surveillance, prevention and treatment of malaria.

Among current approaches in malaria diagnoses, those based on polymerase chain reaction (PCR) provide the highest sensitivity at 0.004 to 5 parasites per µl of blood. However, the most common PCR instruments are not portable and, therefore, inaccessible in most rural regions. Giemsa-stained thick and thin blood films are the most sensitive and specific methods available besides PCR. It exhibits sensitivities between 5 to 20 parasites per µL of blood (0.0001% parasitaemia). However, it requires a carefully prepared sample examined by a specialist, in which malaria infected red blood cells (miRBCs) are identified from 100 to 200 microscopic fields under 1000× magnifications. Traveler's kits, like ICT Malaria Pf/Pv®, Parasight®-F, and OptiMAL®, provide travelers rapid and portable tool to perform self-tests in the field. However, they are limited in sensitivity and specificity and, therefore, inadequate for early-stage malaria detection.

In recent years, advances in cell mechanics research tools have enabled the study of mechanical differences between normal RBCs and miRBCs. Upon infection, human RBCs start to lose their biconcave shape and become more spherical in shape. During the asexual erythrocytic stages of malaria parasite life cycle in the host RBC, the stiffness of the cell body is increased by more than ten times, and knob-like protrusions are formed on the cell surfaces starting at the trophozite stage. These protrusions mediate the cytoadhesion behavior of miRBCs to vascular endothelium, which makes the miRBCs sticky. Similar to human malaria, the avian miRBCs lose their oval shape and form furrow-like structures on cell surfaces similar to human malaria. The cytoadhesion behaviors of miRBCs have been studied with microfluidic devices that mimic the microcirculation environment in living tissues. By culturing vascular endothelium or coating purified receptors in the microfluidic channels, the adhesion probabilities of normal RBCs and miRBCs were almost the same under 20 mPa shear stress. However, normal RBCs rapidly detached from the substrate once the wall shear stress was elevated above this value. At least three mechanical biomarkers could potentially be used to diagnose malaria including: (1) elevated stiffness of the cell body, (2) altered cell morphology, and (3) increased adhesiveness to appropriately treated microchannel surfaces. The present invention addresses the third option of exploiting the increasing adhesiveness of miRBCs to detect malaria infection.

SUMMARY

In one embodiment of the invention, a method of identifying infection by the malaria parasite includes obtaining a sample of RBCs from a subject, flowing the sample through a microfluidic device having a channel comprising a contact surface at a flow rate sufficient to produce a shear rate between about 2.1 sec$^{-1}$ and 3.2 sec$^{-1}$, and identifying the presence of infected RBCs at least temporarily trapped on the contact surface. The contact surface is at least one of hydrophilic and roughened. It some embodiments, the contact surface may be both hydrophilic and roughened.

In another embodiment of the invention, a method of identifying infection by the malaria parasite includes obtaining a sample of RBCs from a subject, flowing the sample at a first flow rate through a microfluidic device having a channel comprising a contact surface being at least one of hydrophilic and roughened, wherein infected RBCs are substantially trapped on the contact surface and wherein non-infected RBCs continue to flow through the microfluidic device. The number of non-infected RBCs in at least a portion of the sample flowing through the microfluidic device are counted. The flow rate through the microfluidic device is then increased and the number of infected RBCs in at least a portion of the sample flowing through the microfluidic device are counted. As in the prior embodiment, in some instances, the contact surface may be both hydrophilic and roughened.

In another embodiment, a device for identifying infection by the malaria parasite includes a microfluidic device having an inlet and an outlet and a diagnostic channel interposed between the inlet and the outlet, the diagnostic channel comprising a contact surface being at least one of hydrophilic and roughened; and a sample pump configured to pump a RBC-containing sample into the inlet. Again, in some instances, the contact surface may be both hydrophilic and roughened.

DETAILED DESCRIPTION OF THE ILLUSTRATED EMBODIMENTS

Figure 1:
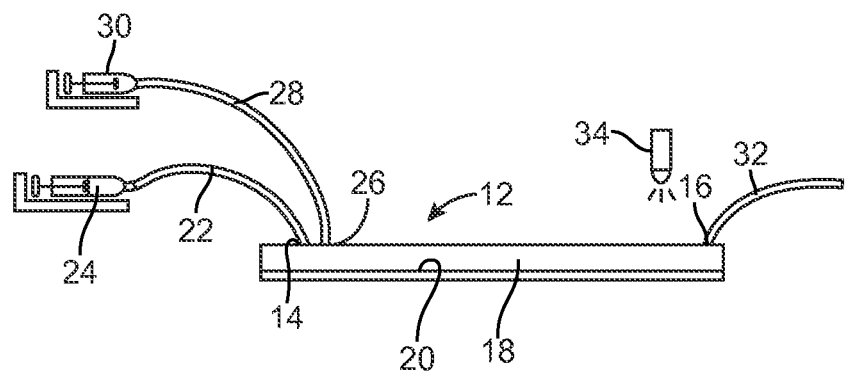
FIG. 1 illustrates one embodiment of a system for identifying infection by the malaria parasite.

FIG. 1 illustrates one embodiment of a system 10 for identifying infection by the malaria parasite. The system 10 includes a microfluidic device 12 that includes at least one inlet 14 and at least one outlet 16 with a diagnostic channel 18 interposed there between. The diagnostic channel 18 includes a contact surface 20 that is typically the bottom surface on which RBCs interact with. The contact surface 20 is used to leverage the surface properties of malaria infected RBCs for capture and ultimate detection and diagnosis. More specifically, the contact surface 20 is used to capture miRBCs based on two distinct surface properties of miRBCs. A first surface property of miRBCs that is used includes the fact that miRBCs have increased cytoadhesive properties (e.g., stickiness) as compared with non-infected RBCs. The second property used in the system 10 is that miRBCs are generally rougher than health RBCs. This increased roughness is caused by morphological changes in the cell membrane of miRBCs.

The contact surface 20 may be modified to leverage one or both of these surface properties of miRBCs. For example, the contact surface 20 may be hydrophilic which allows the miRBCs to have a higher probability or chance of sticking to the contact surface 20 as compared to non-infected RBCs. The contact surface 20 may, alternatively, or in addition to, be roughened which allows the roughened miRBCs to experience higher friction than smooth, healthy RBCs while the miRBCs touch the surface. This slows down (or completely stops) the speed at which miRBCs travel down the diagnostic channel 18. Thus, in some embodiments the contact surface 20 may be hydrophilic. In other embodiments, the contact surface 20 may be roughened. In still other embodiments, the contact surface 20 may be both hydrophilic and roughened.

The diagnostic channel 18 may have a number of configurations. Typically, the diagnostic channel 18 has a square or rectangular cross-sectional profile. For example, the diagnostic channel 18 may have a width of a few hundred micrometers (e.g., 340 μm), a height of less than 100 micrometers (e.g., 50 μm), and a length that is more than about 10 mm (e.g., 11 mm) The longer length of the diagnostic channel 18 provides more opportunity for the miRBCs to interface with the contact surface 20 and therefore improves the sensitivity of the system 10.

As seen in FIG. 1, the inlet 14 is coupled to a conduit 22 that connects to a sample pump 24. The sample pump 24 may include any number of types of pumps including, for example, a syringe pump as illustrated in FIG. 1. The sample pump 24 is used to pump a fluid sample containing RBCs into the microfluidic device 12. The sample pump 24 is preferably configured to pump the fluid sample through the diagnostic channel 18 at multiple flow rates. As explained herein, in one embodiment, it is preferable to pump the RBC-containing sample through the microfluidic device 12 at a flow rate sufficient to produce a shear rate between about $2.1\ sec^{-1}$ and $3.2\ sec^{-1}$.

Still referring to FIG. 1, in some embodiments, there may be an optional secondary inlet 26 that is coupled to a conduit 28 that connects to a secondary pump 30. The secondary inlet 26 may be used to introduce a perfusion fluid into the microfluidic device 12 as explained below. Alternatively, the secondary inlet 26 may be used to introduce a fluid generating a sheath flow around the RBC-containing sample that flows through the microfluidic device 12. The secondary pump 30 is preferably configured to pump the fluid sample (e.g., perfusion or sheath flow fluid) through the diagnostic channel 18 at multiple flow rates. The outlet 16 is coupled to a conduit 32 that may be used to direct the sample to a collection reservoir or waste reservoir.

FIG. 1 illustrates an optical interrogator 34 that may be optionally used as part of the system 10. The optical interrogator 34 is used to count the cells that flow past a field-of-view (FOV) within the diagnostic channel 18. The optical interrogator 34 is preferably configured to count the number of RBCs passing through the FOV. Preferably, the optical interrogator 34 is able to count both miRBCs and non-infected RBCs. In this regard, the system 10 is able to calculate the infection rate of the sample. The optical interrogator 34 may be operatively coupled to a computer (not shown) or the like that acquires and processes data to count cells passing there through. The computer may also be used to calculate the infection rate of the sample based on the percentage of miRBCs detected during interrogation. The optical interrogator 34 may image unstained or in some instances stained cells. It is preferably, however, that the optical interrogator 34 image the cells without the need to stain the RBCs so as to avoid the additional processing step (and expense) of adding a stain.

Figure 2:
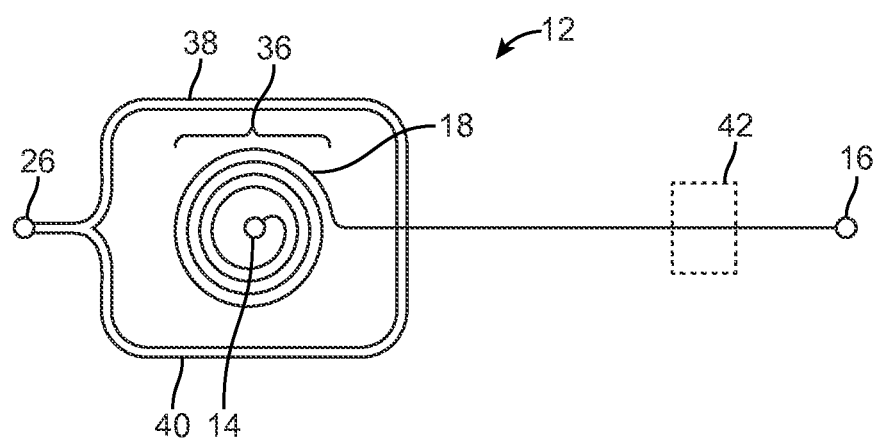
FIG. 2 illustrates another embodiment of a microfluidic device for use in a system for identifying infection by the malaria parasite.

FIG. 2 illustrates one embodiment of the system 10. FIG. 2 illustrates a top-down plan view of the configuration of the microfluidic device 12. The microfluidic device 12 includes a first inlet 14 that is used to deliver the RBC-containing sample to the microfluidic device 12. For example, the first inlet 14 may be coupled to a sample pump 24 via a conduit 22 as illustrated in FIG. 1. The first inlet 14 is coupled to a diagnostic channel 18 that includes a spiral section 26 that gives added length within a relatively small "footprint" in the microfluidic device 12. The spiral section 36 of the diagnostic channel 18 includes a contact surface that is used to capture the miRBCs. The non-infected RBCs, however, continue downstream the diagnostic channel 18. As seen in FIG. 2 there is a second inlet 26 that connects to first and second sheath flow conduits 38, 40. The sheath flow conduits 38, 40 carry sheath flow fluid that is delivered via a secondary pump such as pump 30 illustrated in FIG. 1. The sheath flow conduits 38, 40 intersect with the diagnostic channel 18 downstream of the spiral section 36. The sheath flow conduits 38, 40 deliver sheath fluid to either side of the diagnostic channel 18 to pinch or focus the RBC cells within the center of the diagnostic channel 18. By centering or focusing the RBC cells within the diagnostic channel 18, the RBCs can be better counted downstream by the optical interrogator 34.

Still referring to FIG. 2, an optical interrogation region 44 is located in a downstream portion of the diagnostic channel 18. The optical interrogation region 44 is wherein the optical interrogator 34 counts the miRBCs and non-infected RBCs passing by. The diagnostic channel 18 continues until the outlet 16 is reached. The height of the diagnostic channel 18 and the sheath flow conduits 38, 40 may be equal. For example, the height may be less than 100 μm. As seen in FIG. 2, the sheath flow conduits 38, 40 have a width that is larger than the width of the diagnostic channel 18. In the embodiment of FIG. 2, the width of the sheath flow conduits 38, 40 is around three times the width of the diagnostic channel 18. For example, the sheath flow conduits 38, 40 may have a width of around 300 μm while the diagnostic channel 18 has a width of around 100 μm.

In the operation of the microfluidic device 12 of FIG. 2, a RBC sample from a subject may be flowed into the diagnostic channel 18 at first flow rate. The flow rate is at a level such that miRBCs are substantially trapped on the contact surface 20 and wherein the non-infected RBCs continue to flow down the diagnostic channel 18. These non-infected RBCs can then be focused downstream using sheath flow and counted using the optical interrogator 34. The flow rate can then be increased through the diagnostic channel 18 such that the captured or trapped miRBCs are then carried down the diagnostic channel 18. The miRBCs are focused downstream using sheath flow and counted using the optical interrogator 34.

The microfluidic device 12 may be made by bonding a micromolded polydimethylsiloxane (PDMS) chamber onto a hydrophilic substrate such as glass. The glass may be roughened by acid treatment (e.g., HF acid treatment) or it may be roughened by other processing steps (e.g., mechanical roughening). Particular details regarding the manufacture of the microfluidic device 12 are described in more detail herein.

Figure 3A:
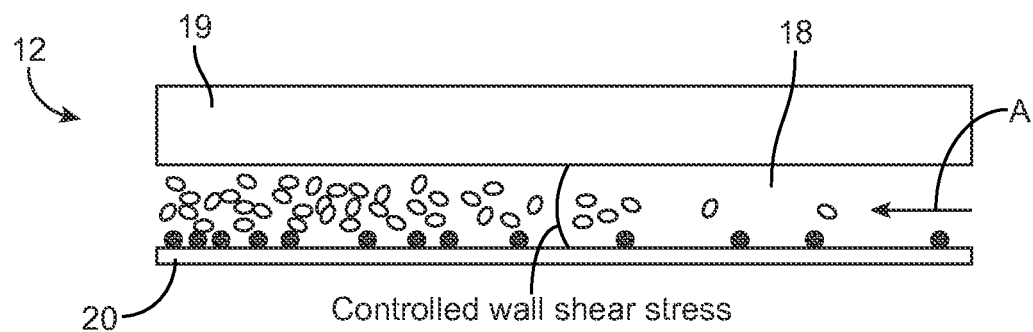
FIG. 3A illustrates a cross-sectional view of a microfluidic device according to one embodiment. The cross-section is taken along a line passing through the diagnostic channel.
Figure 3B:
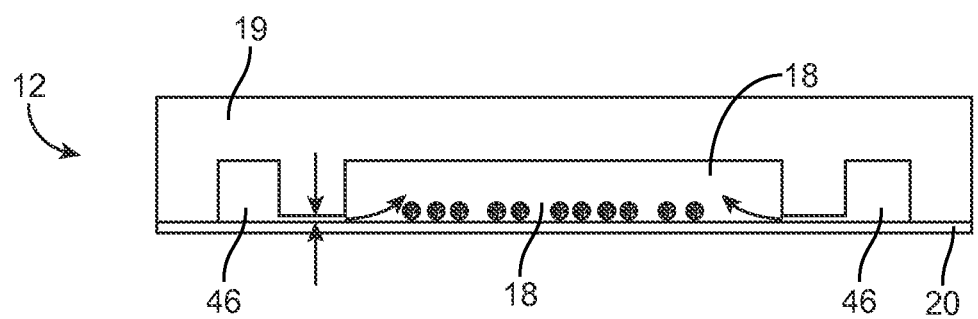
FIG. 3B illustrates a cross-sectional view of the microfluidic device taken along a direction substantially perpendicular to the cross-section of FIG. 3A.

FIGS. 3A and 3B illustrate a microfluidic device 12 that was used to test the capture of malaria infected avian red blood cells (miaRBCs). The microfluidic device 12 includes a long and thin diagnostic channel 18 that is formed between PDMS top 19 and the contact surface 20. Two versions of the microfluidic device 12 were developed with varying lengths (11 mm and 100 mm) The diagnostic channel 18 had a depth of 50 μm. The diagnostic channel 18 was made by bonding a micromolded PDMS channel onto a 170 μm thick glass cover slide which acted as the contact surface 20 (explained more in detail below). The glass cover slide provided a contact surface 20 for capturing miaRBCs, and the PDMS chamber formed hydrophobic chamber to prevent miaRBCs from sticking to the chamber walls. To capture miaRBCs in the blood sample, a fully developed fluid flow was created (illustrated in direction of arrow A) and maintained in the diagnosing channel 18. The wall shear stress was approximately 25 mPa.

The platform of FIGS. 3A and 3B was designed to prevent cells from clotting inside the diagnostic channel and to increase the probability of miaRBCs interacting with the hydrophilic substrate. Under this controlled flow field normal avian RBCs (aRBCs, white ovals in FIGS. 3A and 3B) readily flowed away from the diagnostic channel. Conversely, the miaRBCs (gray ovals in FIGS. 3A and 3B) carried by the fluid flow rolled on the hydrophilic substrate due to their adhesive cell surfaces. These miaRBCs eventually reduced their speed and adhered to the substrate. After all the normal cells flow away from the diagnostic channel, the number of miaRBCs was identified on the hydrophilic surfaces and the stage of infection was diagnosed by calculating the number of captured miaRBCs.

The specificity and sensitivity of the system 10 depends on three design parameters. First, the chamber depth of the diagnosing channel 18 had to be designed to increase the possibility of miaRBCs interacting with glass substrate while still providing enough space for normal cells to flow away from the chamber. This was the reason why the chamber depth was chosen to be 50 μm, which is about five times larger than the characteristic length of a normal aRBC. Second, the length of the diagnostic channel had to be long enough to capture all the miaRBCs. This was because only the miaRBCs close to the hydrophilic substrate could be captured. A sufficiently long interaction path was necessary for a miaRBC to adhere to the substrate, where more miaRBCs were captured downstream of the chamber. Third, the total volume of blood sample screened determined the sensitivity of early stage blood sample. The limitation of the blood film, which is considered to be the gold standard, is the need to inspect 100 to 200 microscopic fields manually under 1000× magnifications. By using the adhesive behavior of miaRBCs as the biomarker, the designed platform can efficiently screen 1 μl blood by flowing through the diagnosing channel 18, and the sensitivity can also be enhanced by increasing the total blood volume. One important factor is that the cyto-adhesion of miaRBCs becomes more active as malaria progresses from the asexual erythrocytic stage to the trophozoite stage. The miaRBCs become even stickier by the end of the schizont stage. During the first few hours of infection in the ring stage, the miaRBCs might not have enough adhesive forces to resist the fluid flow.

Still referring to FIGS. 3A and 3B, in order to verify that the captured cells were all miaRBCs, two perfusion channels 46 were designed next to the diagnostic channel 18 with a 2 μm shallow openings between two of them (seen in FIG. 3B). This provided a high flow resistance into the diagnostic channel 18, and mass transport was dominated by diffusion. This geometrical barrier provided a means to stain the captured miaRBCs with Giemsa without any mechanical perturbation during perfusion. The volume of the perfusion channels 46 was intentionally designed several times smaller than the diagnostic channel 18. These two perfusion channels 46 played two important roles in this design. First, the perfusion channels 46 can be used to slowly dilute the anticoagulant agent (heparin) during cell loading, and completely flushed the plasma after the normal cells flow out of the chamber. Removing heparin from the sample was necessary because it would otherwise suppress the cyto-adhesion capability of miaRBCs. Second, the perfusion channels could be used to introduce Giemsa stain into the diagnostic channel and stain the captured miaRBCs. Due to the slow diffusion rate by design, parasites in the host RBCs were stained much faster than the nuclei of RBCs. This minimized the possible confounding dark area from the stained nuclei, and enhanced the clarity of malaria parasites identifications. The excess stain could then be removed by introducing fresh media again once the stain is completed. Subsequently, the captured cells were visually verified with a 100× oil lens through the 170 nm thick glass cover slide.

It should be understood that the perfusion channels 46 may be optional and removed entirely from the microfluidic device 12. For instance, the microfluidic device 12 of FIG. 2 does not have any perfusion channels 46.

Figure 4A:
FIGS. 4A-4E illustrate an illustrative method of forming a microfluidic device according to one embodiment.
Figure 4A:
Figure 4B:
Figure 4C:
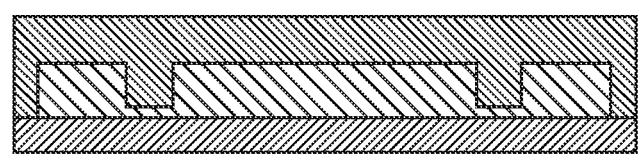

FIGS. 4A-4E illustrate the microfabrication steps of for the microfluidic platform illustrated in FIGS. 3A and 3B for malaria diagnosis. The PDMS microchannel was microfabricated based on standard PDMS micromolding. The SU-8 mold was made using a technique similar to that described in Hung et al., A novel high aspect ratio microfluidic design to provide a stable and uniform microenvironment for cell growth in a high throughput mammalian cell culture array, Lab Chip 5: 44-48 (2005), which is incorporated by reference herein. A (100) silicon wafer was cleaned with standard RCA 1 cleaning and a five-minute dip in 2% HF, followed by 30 minutes of oven dehydration at 120° C. A layer of 2 μm thick SU-8 2002 negative photoresist (Micro Chem) was spun onto the cleaned wafer. Standard photolithography process was used to create the mold for the 2 μm shallow openings between perfusion channels and diagnostic channel (FIG. 4A). A second layer of SU-8 50 negative photoresist (Micro Chem) was spun over this 2 μm mold, and perfusion channels 46 and diagnostic channel 18 were then created by the second photolithography step (FIG. 4B). The developed SU-8 mold was finalized by hard baking at 175° C. for 30 minutes. Before casting PDMS, the SU-8 mold and silicon wafer surfaces were silanized with trichlorosilane ($C_8H_4Cl_3F_{13}Si$) in a vacuum chamber. A 10-to-1 ratio PDMS prepolymer and curing agent (Sylgard 184, Dow Corning) was then casted on the SU-8 mold to create a 2-mm thick PDMS layer (FIG. 4C).

Figure 4D:
Figure 4E:

After degassing under vacuum, the PDMS was cured in a 65° C. oven over night and de-molded in a laminar flow hood (FIG. 4D). An 18 G needle was used to create 1-mm-diameter holes for inlets and outlets. This PDMS layer and a clean 170 μm thick cover glass slide were plasma treated in an air plasma (Harrick Scientific, NY) at 200 mTorr and 200 Watts for 5 minutes. These components were then quickly brought into contact and placed into a 65° C. oven for 5 minutes to complete the microfluidic platform (FIG. 4E).

As explained above, there are two designed microfluidic platforms for the study of malaria diagnosis. The chamber depth of both microplatforms was 50 μm, and the total lengths of diagnostic channels were 11 mm and 100 mm, respectively. The widths of the perfusion channels and diagnostic channel of microplatform #1 are 50 μm and 350 μm, respectively. Those for microplatform #2 are 100 μm and 200 μm, respectively.

Two experimental setups were conducted to study the feasibility of using the adhesive behavior of miaRBCs as a biomarker for malaria diagnosis. To verify the possibility of using a hydrophilic substrate to capture miaRBCs, an avian blood sample with 20.1% malaria infection was chosen. The infection percentage was verified by the standard blood film method while the sample was drawn from host chicken. This sample was originally frozen in Hank's buffered saline mixed with heparin anticoagulant and 20% glycerol. Thus, the concentration of cells was diluted by half The sample was thawed at room temperature right before loading into the diagnostic channel. The whole experiment was performed on top of an Olympus 1X51 inverted microscope with a Hamamatsu high resolution CCD camera under room temperature.

Figure 5A:
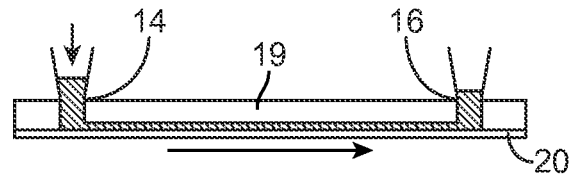
FIGS. 5A-5F illustrate the blood sample loading sequence used to capture miaRBCs starting with filling diagnostic channel with fresh media (FIG. 5A); add blood sample (FIG. 5B), flow blood sample into chamber (FIG. 5C), wait until blood sample fill up the chamber (FIG. 5D), add media to reverse the flow and create a slow flow rate (FIG. 5E), and inspect captured miaRBCs after plasma and normal cells been pushed away (FIG. 5F), and inlet and outlet are located on the left and right hand sides, respectively
Figure 5B:
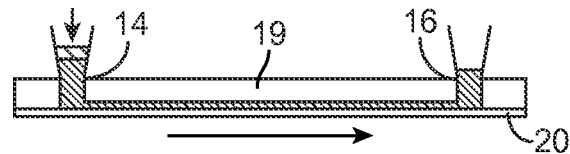

FIGS. 5A-5F illustrate the loading sequence of the diagnostic channel, where the arrows below each respective FIG. represent the flow rate and its direction. Four 200 μl pipette tips were first plugged into punched holes of the inlets and outlets of the microfluidic device 12 of the type illustrated by FIGS. 3A and 3B. Then the perfusion channels 46 were filled with 50 μl fresh $CO_2$ independent culture media (Gibco™, Invitrogen Co.) with 1% penicillin/streptomycin and 4 mM L-glutamine using a pipette. The pipette was removed after 10 μL media reached the pipette tip at the outlet (not shown). This created a continuously steady media flow in the perfusion channels 46, which slowly replaced the thawed frozen solution, plasma, and anticoagulant agent with fresh media. Then, the diagnostic channel was also filled with 50 μl fresh media until 10 μl reached the other side (FIG. 5A), followed by the addition of 20 μl thawed blood sample at the inlet (FIG. 5B).

Figure 5C:
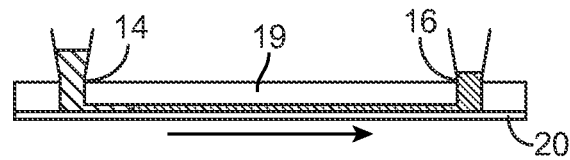
Figure 5D:
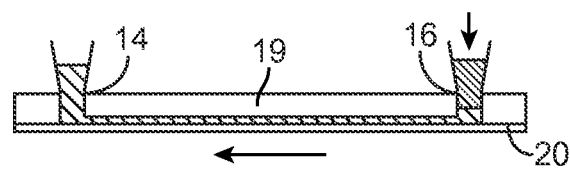
Figure 5E:
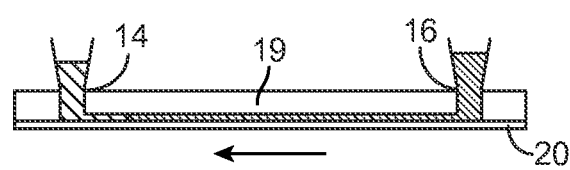
Figure 5F:
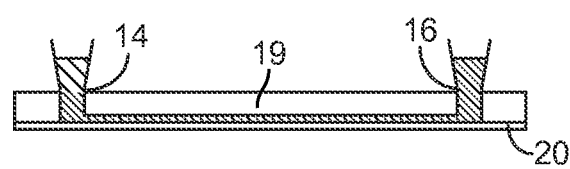

This further diluted the concentration of cells by one-third. The added blood sample was quickly mixed with media by diffusion and flowed into the diagnostic channel (FIG. 5C). The outlet of the diagnostic channel 18 was monitored during the cell loading. Another 50 μl media was added to the pipette tip at the outlet once the cells arrived (FIG. 5D). This ceased the flow and controlled the total volume of loaded blood sample, which was about 0.2 μl. The loaded cells were then slowly flowed back by adding additional media to create 1.0 to 1.5 mm $H_2O$ pressure difference, and miaRBCs were allowed to interact with the hydrophilic substrate (FIG. 5E). The loaded normal cells were slowly flowed out of the diagnosing channel and the fluid flow was stopped at the time the potential difference decreased to zero (FIG. 5F). The media of diagnostic channel was also replaced with fresh culture media during this process through the perfusion channels. The last step was to add another 52 μl state stain in the outlet of the perfusion channel (not shown), and stained captured cells. Captured cells were then investigated with a 1000× oil lens to identify stained parasites.

In order to study the interaction between miaRBCs and the hydrophilic surface, a controlled wall shear stress was applied to the microplatform #2 by using a NE-1000 programmable syringe pump (New Era Pump System, Inc.). A frozen avian blood sample with 7.8% malaria infection was used in this experiment. The volume flow rate was controlled at 0.03 μl/mm to create a wall shear stress of around 60 mPa. This estimation was based on the analytical solution of developed laminar flow of a fluid with the viscosity of blood at this specific flow rate between two parallel plates. This value was chosen because it has been previously reported that 10% to 30% adhered miaRBCs were washed out in this range. By flowing blood sample under this condition, it was observed that the miaRBCs gradually slowed down and contacted the hydrophilic substrate along the diagnostic channel 18. The 100 mm long diagnostic channel 18 allowed a long enough path for cells to interact with the substrate.

Figure 6A:
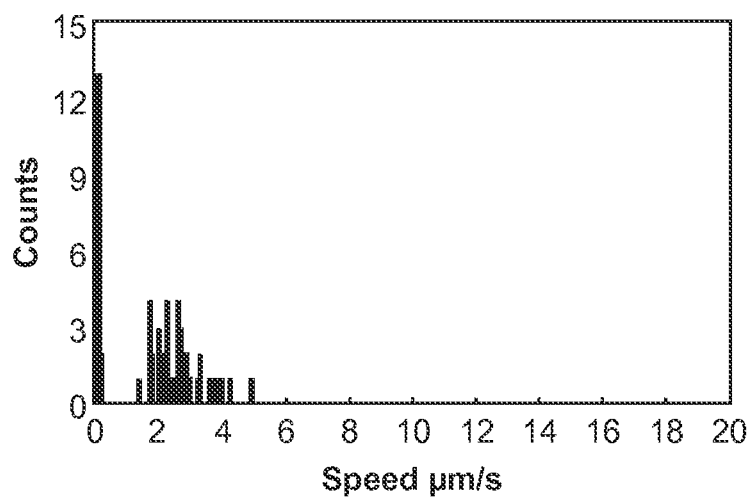
FIG. 6A illustrates the distribution of cell speed of fifty traced miaRBCs in microplatform #1.
Figure 6B:
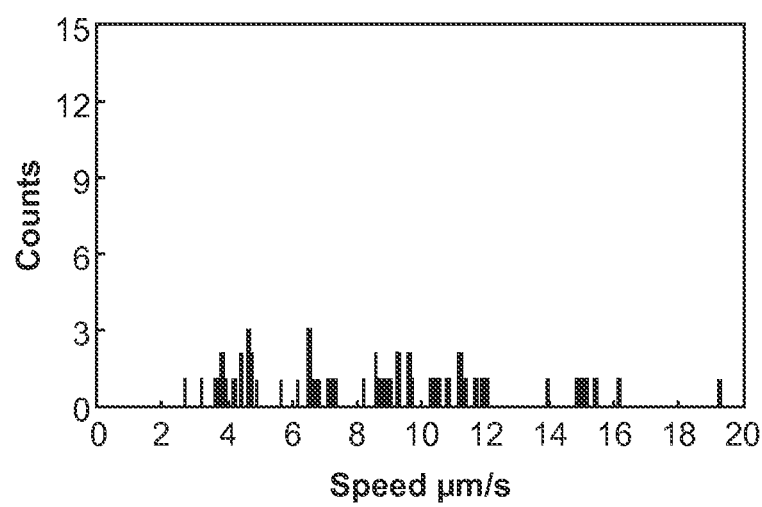
FIG. 6B illustrates the distribution of cell speed of fifty traced non-infected aRBCs in microplatform #1.

FIGS. 6A and 6B illustrate, respectively, the flow speeds of miaRBCs and non-infected RBCs in microplatform #1 fifteen minutes after loading. The data points were taken from five 400× fields at different locations along the diagnostic channel, and a random selection of fifty cells for normal and infected cells from each field were traced. It is clear from FIG. 6A that thirteen (13) out of 50 miaRBCs were already immobilized and the speed of others were reduced to about 3 μm/s. As seen in FIG. 6B, normal RBC cells were evenly distributed throughout the depth of the chamber, and there were no normal cells adhered to the substrate. The estimated shear stress was around 25 mPa calculated from the flow speed of the RBCs and the viscosity of blood at this flow rate. This value matched the reported data that normal cells follow the fluidic flow under a shear stress higher than 20 mPa. This experiment demonstrated that the miaRBCs could interact with a hydrophilic surface and adhere on it if the shear stress from the sample flow was close to 20 mPa.

Figure 7A:
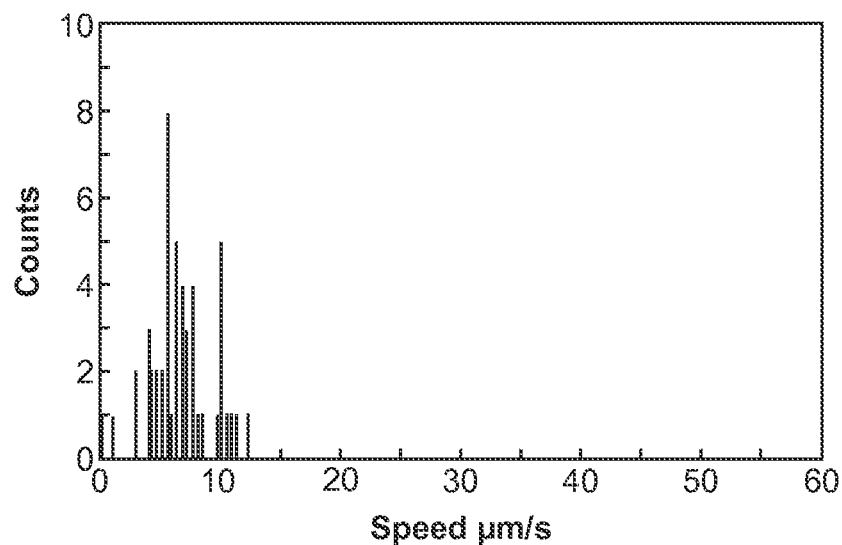
FIG. 7A illustrates the distribution of cell speed of fifty traced miaRBCs in microplatform #2.
Figure 7B:
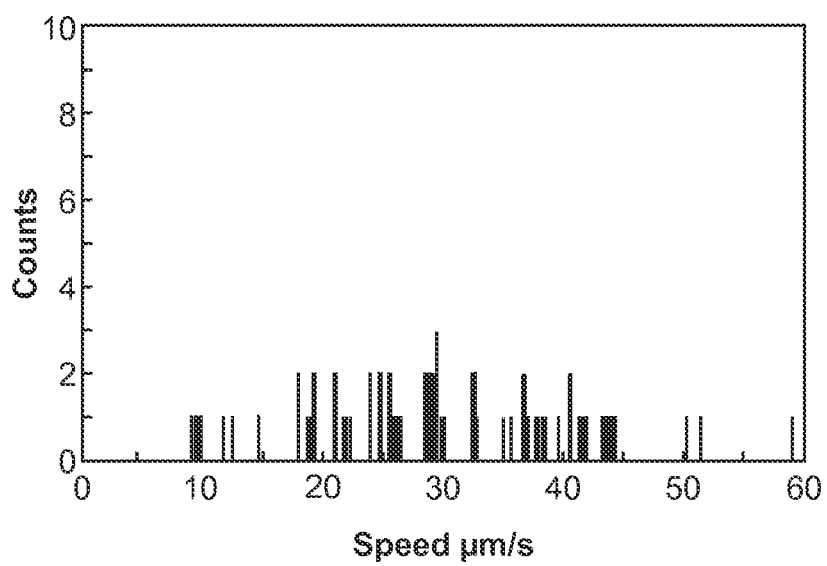
FIG. 7B illustrates the distribution of cell speed of fifty traced non-infected aRBCs in microplatform #2.

FIGS. 7A and 7B illustrate the experimental results of microplatform #2 twenty minutes after continuously flowing blood sample into diagnostic channel. FIG. 7A illustrates the tracing of 50 miaRBCs while FIG. 7B illustrates the tracing of 50 non-infected RBCs. FIG. 7A shows that under this flow condition, the distribution of flow speed of miaRBCs was below 15 µm/s. Normal aRBCs were evenly distributed from 9 to 60 µm/s. Furthermore, the percentage of infected cells, originally at 7.8%, was increased to 8.82%. This indicated that the adhesive behavior of miaRBCs resulted in a drag force exerted between the miaRBCs and the hydrophilic substrate. This force gradually caused the miaRBCs to reduce their speed and could become immobilized and adhered to the substrate if the adhesive force can resist shear flow. One miaRBCs out of 50 infected cells were captured. This implied that the flow rate of blood samples inside the diagnostic channel must be controlled to maintain a wall shear stress that does not dislodge adhered miaRBCs while allowing normal aRBCs to flow through. Furthermore, this controlled shear stress would also determine the sensitivity and specificity since the percentage of captured miaRBCs is highly dependent on the flow condition.

In another set of experiments, the microfluidic device of FIGS. 3A and 3B was tested with various roughened glass substrates (Corning No. 1) and infected (*Plasmodium gallinaceum*) and non-infected avian RBCs. Three different such glass substrates were tested with varying degrees of exposure to hydrofluoric (HF) acid. This includes (1) the untreated condition, (2) treated with 2% HF for 1 min, and (3) treated with 10% HF for 2 min, respectively. AFM measurements showed that the root-mean-squared (rms) surface roughness quantities were 0.1892 nm, 0.3988 nm, and 2.3286 nm, and the ten-point-heights were 2.0991 nm, 3.1988 nm, and 14.7238 nm, respectively. These glass substrates offered nano-scale protrusions close to the dimensions of surface lesions and furrow-like structures of the miaRBCs.

A fully developed fluid flow was created and maintained in the diagnostic channel with a well-controlled fluid introduction sequence. This was designed to prevent cells from clotting inside the diagnostic channel while maximizing the probability of interaction between miaRBCs and the substrate. Under a range of controlled flow fields, it was observed that the great majority of non-infected RBCs readily flowed away from the diagnostic channel. On the contrary, the miaRBCs carried by the fluid flow rolled and reduced their speeds when they interacted with the roughened surface, and were finally immobilized at locations throughout the channel. After all the normal cells flowed away from the diagnostic channel, the number of captured miaRBCs was visually identified and the stage of infection was determined by calculating the projected ratio of miaRBCs to non-infected RBCs. The low affinity of smooth non-infected aRBCs to roughened substrate was verified by flowing normal RBCs onto the platform with similar substrate under identical wall shear rates. The immobilization efficiency and sensitivity were quantified by total number of non-infected RBCs or miaRBCs captured versus total number of cells loaded.

FIGS. 5A-5F illustrate the loading sequence of the diagnostic channel as previously described herein. This protocol was developed to control the total volume and concentration of blood sample loaded and to prevent blood clotting throughout the process. It also significantly minimized loss of RBCs due to gradual precipitation and coagulation in the dead volume of the fluid pipeline, such as the syringe in the syringe pump, where there is no agitation source. Four 200 µl pipette tips were first snuggly inserted into the inlets and outlets of the diagnostic channel and the perfusion channels (not shown).

The perfusion channels and diagnostic channel were then filled with 80 µl fresh media through the inlet of the perfusion channels. The injection was performed until the media level of all four pipette tips reached similar heights and all air bubbles were flushed out (not shown). This platform was then left on the microscope stage to allow the media levels to equalize, at which point each tip would have 20 µl of media. This process took about 10 min. The media was prepared with $CO_2$-independent culture media (Gibco™, Invitrogen Co.) consisting of 1% penicillin/streptomycin and 4 mM L-glutamine. Heparin coated capillary tube was used to collect blood from chicken infected with the *P. gallinaceum* parasites. The infection percentage of the blood samples was verified with a standard blood film method. A measured volume of 10 µl of blood sample was carefully mixed with 70 µl CO2-independent culture media. Seventy-five µl of this mixture was gently and slowly mixed into the 20 µl media in the pipette tip positioned in the inlet of the diagnostic channel with gel loading tips. This step diluted the blood sample to 10% v/v and allowed RBCs to spread evenly in the diagnostic channel into a monolayer, maximizing the likelihood for each cell to interact with the substrate. Further, the dependency of shear rate on blood viscosity was also minimized in the diluted blood sample. The concentration was calculated based on the normal cell count of avian blood, which is about 2.58 million RBCs per microliter of blood.

The pipette tip at the diagnostic channel inlet, which at this point contained 95 µl of diluted blood sample, resulted in a hydrostatic pressure difference in reference to the 20 µl media in the pipette tip at the outlet. The loaded RBCs then flowed into the diagnostic channel under this differential pressure (FIG. 5B). At the same time, another 75 µl culture media was added to the inlet of the perfusion channels to suppress any pressure gradient between the perfusion channels and the diagnostic channel. The purpose of this step was to prevent the loss of normal RBCs, which could be pushed out to the perfusion channels through the 2 µm shallow openings with their deformable cell bodies. In addition, this created a continuous and steady fluidic flow in the perfusion channels, replacing plasma and anticoagulant agent in the diagnostic channel with fresh media through diffusion from the perfusion channels. The loaded RBCs flowing into diagnostic channel were then monitored and followed under the microscope (FIG. 5C). Once the RBCs reached the outlet of the diagnostic channel, different volumes of media were added to the pipette tip at the outlet to achieve controlled reverse flow. It was during the reverse flow that the relationship between the immobilization efficiency and the shear rates was studied (FIG. 5D).

An identical amount of DAPI fluorescent stain at 1 mg/ml in PBS was simultaneously added to the outlet of perfusion channels to both balance the pressure and also stain the captured miaRBCs. This step created a controlled hydrostatic potential difference between the inlet and outlet of the diagnostic channel and reversed the flow with a controlled wall shear rate. The optimized pressure difference was 1.0 to 1.5 mm $H_2O$. The final volume of media and DAPI solution added to the outlets was 85 µl. Since the volume of the diagnostic channel was only 0.19 µl, the wall shear rate can be controlled within a reasonably tight tolerance to effectively flush the non-infected RBCs from the channel while allowing miaRBCs to interact with the roughened substrate as seen in FIG. 5E. The total number of cells loaded was estimated to be around 51,000.

Finite-element simulation with COMSOL Multiphysics 3.5a was used to estimate the induced shear rate. Based on the simulation results, the wall shear rates were calculated to be between 2.1 s$^{-1}$ to 3.2 s$^{-1}$. It was observed that, under low flow rates, blood clotting could gradually develop at locations close to the diagnostic channel inlet if the blood sample was insufficiently diluted to the point that the resulting concentration was higher than 15% v/v. This condition would decrease and eventually impede fluidic flow. In this case, the developed wall shear rate could not be maintained for a period long enough for all the non-infected RBCs to flow out of the diagnostic channel. This condition was avoided in this experiment with 10% v/v dilution of the blood sample.

Figure 9A:
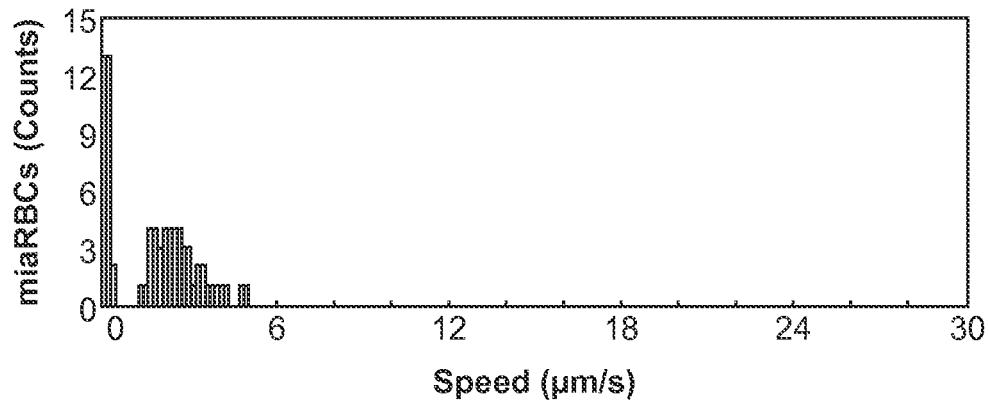
FIG. 9A illustrates the distribution of cell speed of fifty traced miaRBCs under a wall shear rate of $2.14\ s^{-1}$.
Figure 9B:
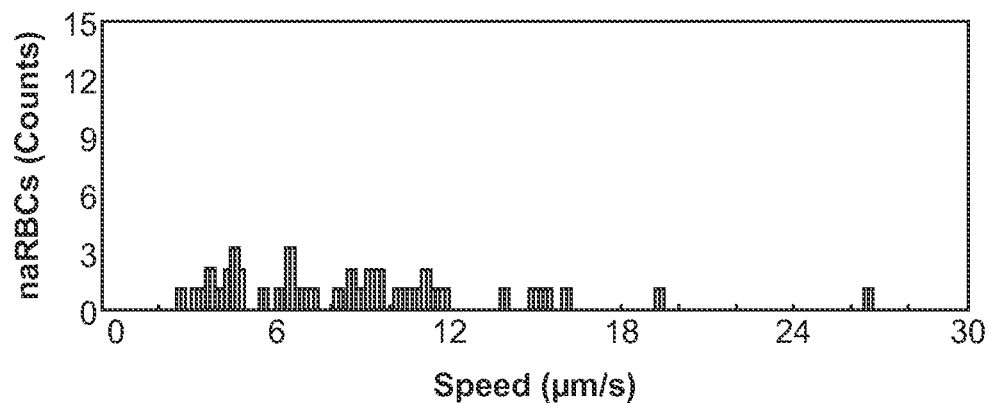
FIG. 9B illustrates the distribution of cell speed of fifty traced non-infected aRBCs under a wall shear rate of $2.14\ s^{-1}$.

As the non-infected RBCs flowed out of the diagnostic channel, the fluid inside the channel was flushed with the remaining media until the hydrostatic potential difference decreased to zero (FIG. 5F). The overall process was performed under continuous flow to prevent clotting and was completed within 30 min, which was short enough to preserve the natural RBC characteristics. Once the captured miaRBCs were stained with DAPI fluorescent stain, they were then visually identified and quantified with a 100× oil lens under 1000× total magnification. The whole experiment was performed on an Olympus 1X51 inverted microscope with a Hamamatsu high resolution gray scale CCD camera at room temperature. Identical procedures were conducted with non-infected aRBCs to investigate their immobilization rate on roughened substrate as the control.

that one of the 50 miaRBCs became immobilized on the substrate. It was also found that the percentage of infected cells, determined to be 7.8% with standard blood film method prior to this experiment, was observed to be 8.82% per image field. FIGS. 9A and 9B show the measured flow speeds of miaRBCs and non-infected aRBCs under 2.14 s$^{-1}$ wall shear rate at 15 min after loading. FIG. 9A shows that 13 out of 50 miaRBCs were already immobilized and the speed of others are reduced to below 5 µm·s$^{-1}$. At the same time, the flow speeds of non-infected aRBCs, again, spread over a much broader range, from 2 to 27 µm·s$^{-1}$ (FIG. 9B), and no non-infected aRBCs were immobilized even at this slower flow rate.

Table 1 below presents a comparison of the immobilization rates of miaRBCs and non-infected aRBCs from fresh blood samples at various infection stages. Healthy blood samples with no infection were included as the control. The flow rates were controlled to be around 2.14 s$^{-1}$, and untreated glass substrates were used. The infection stage was identified by standard blood film method prior to the experiments and was listed as % infection. For the control experiments with fresh, healthy blood samples, 25 to 37 non-infected aRBCs were immobilized on the glass substrate, particularly towards the end of the fluid flow process. Similar numbers of immobilized non-infected aRBCs were observed throughout the entire set of infected blood samples at different infection stages. This could be due to the decreased wall shear rate near the end of the process when a small portion of remaining non-infected aRBCs were still lingering in the diagnostic channel. However, a more careful experiment with a fine control to achieve constant flow speed is needed to verify this speculation. The number of immobilized non-infected aRBCs could potentially be minimized by maintaining a constant flow speed.

|  | Host A | Host B | Host C | Host D | Host E | Host F | Host G |
|---|---|---|---|---|---|---|---|
| % Infection | 0.0% | 0.0% | 3.2% | 3.9% | 9.1% | 13.4% | 20.1% |
| # miaRBCs | 0 | 0 | 55 | 76 | 363 | 977 | 1093 |
| Sensitivity$^a$ | 0.000% | 0.000% | 0.108% | 0.149% | 0.712% | 1.916% | 35.719% |
| Efficiency$^b$ | 0.000% | 0.000% | 3.370% | 3.821% | 7.822% | 14.296% | 17.771% |
| # non-infected aRBCs | 25 | 37 | 20 | 28 | 7 | 16 | 9 |
| Sensitivity$^a$ | 0.049% | 0.073% | 0.039% | 0.055% | 0.014% | 0.031% | 0.029% |
| Efficiency$^b$ | 0.049% | 0.073% | 0.041% | 0.057% | 0.015% | 0.036% | 0.037% |
| Specificity$^c$ | NA | NA | 73.33% | 73.08% | 98.11% | 98.39% | 99.18% |

Figure 8A:
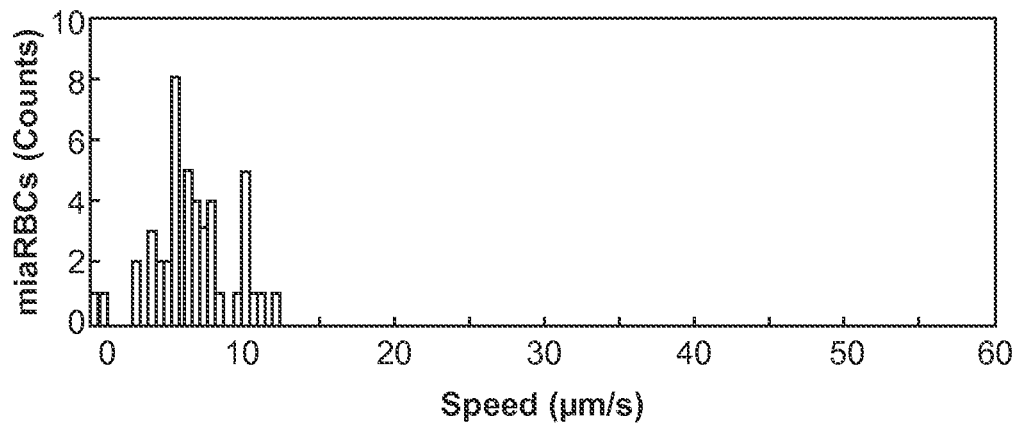
FIG. 8A illustrates the distribution of cell speed of fifty traced miaRBCs under a wall shear rate of $4.70\ s^{-1}$.
Figure 8B:
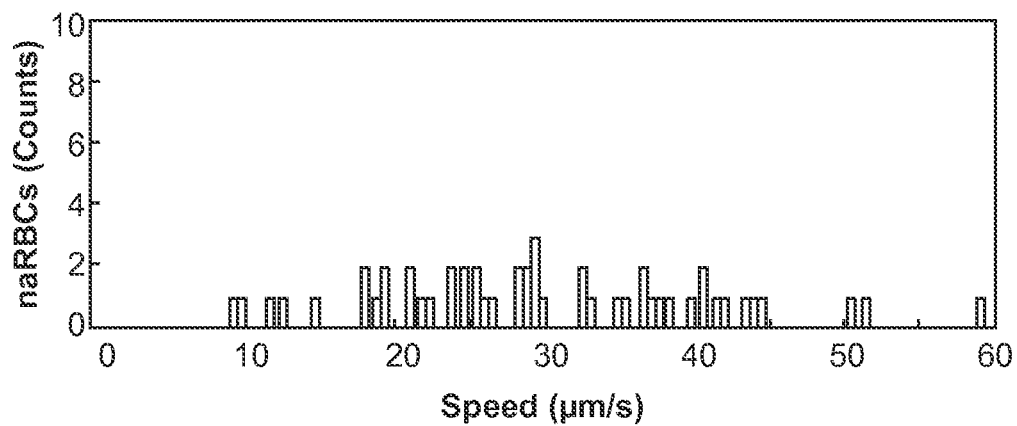
FIG. 8B illustrates the distribution of cell speed of fifty traced non-infected aRBCs under a wall shear rate of $4.70\ s^{-1}$.

$^a$Sensitivity = the number of immobilized cells/total number of loaded cells
$^b$Efficiency = the number of immobilized cells/total number of specific cell type loaded, i.e., miaRBCs or non-infected aRBCs
$^c$Specificity = the number of immobilized miaRBCs/total immobilized cells To investigate the influence of the magnitude of wall shear rates on the degrees of immobilizations of both miaRBCs and non-infected RBCs, different flow rates were applied while cell speeds were traced after steady-state flow was established. FIGS. 8A and 8B illustrate the flow speeds of miaRBCs and non-infected aRBCs under a wall shear rate of 4.70 s$^{-1}$. FIGS. 9A and 9B illustrate the flow speeds of miaRBCs and non-infected aRBCs under a wall shear rate of 2.14 s$^{-1}$. The data points were taken from five 400× fields at different locations along the diagnostic channel, and a random selection of ten miaRBCs and ten non-infected aRBCs from each field were traced. FIGS. 8A and 8B show the distributions of measured cell speeds under 4.70 s$^{-1}$ wall shear rate at 20 min after loading. The flow speeds of the fifty miaRBCs were all below 15 µm·s$^{-1}$, while that of the 50 non-infected aRBCs spread over the range from 9 to 60 µm·s$^{-1}$. Worthy of note is To study the relationship between the numbers of captured miaRBCs to actual infection stage, three parameters were defined and listed in Table 1. The sensitivity to miaRBCs is defined by the ratio of the total number of immobilized miaRBCs divided by the estimated total number of cells loaded, which is about 51,000 cells. The efficiency of capturing miaRBCs is defined by the ratio of total number of immobilized miaRBCs divided by the total number of miaRBCs loaded, which was estimated by multiplying % infection with the total number of loaded cells. Similarly, the sensitivity and efficiency of non-infected aRBCs are also listed. The specificity is defined by the total number of immobilized miaRBCs divided by the total number of captured cells. Among these samples, the blood sample from Host G was under a serious infection of up to 30% 12 h before the experiments. It suffered a large amount of RBC loss and the total cell count was only 60% compared to other samples.

Figure 10A:
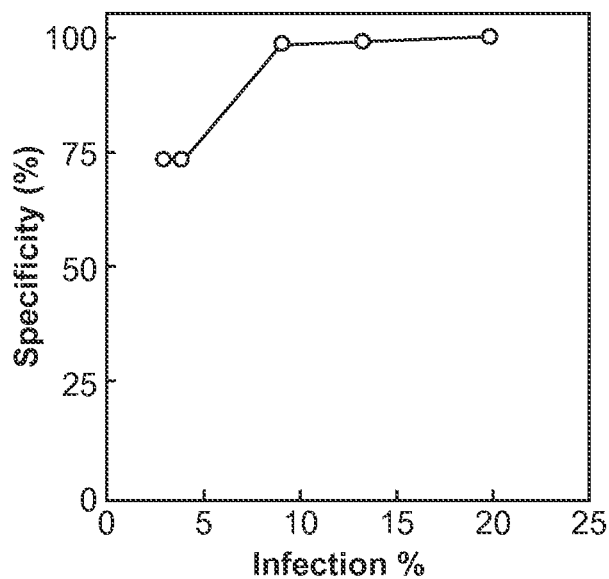
FIG. 10A illustrates the relationship between % infection and immobilization specificity of miaRBCs.
Figure 10B:
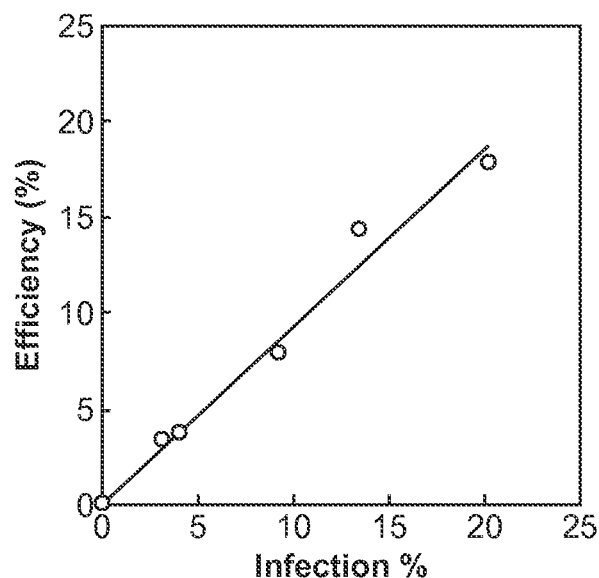
FIG. 10B illustrates the relationship between % infection and immobilization efficiency of miaRBCs.

After studying different blood samples at different infection stages from different host chickens, it was observed that both sensitivity and efficiency of capturing miaRBCs increased with higher % infection. This implies that more miaRBCs reached early trophozoite stage. The specificity is also increased to 99.18% at 20.1% infection, as shown in FIG. 10A. The relatively low sensitivity and specificity of immobilized miaRBCs at low infection stages could be enhanced by increasing the length of the diagnostic channel to maximize the probability of interaction between the miaRBCs and the substrate. Furthermore, a roughly linear relationship was observed between the % infection and the miaRBC immobilization efficiency, as shown in FIG. 10B. The slope of the best-fit line is 0.919, intersecting the y-axis almost at the origin. This is consistent with the assumption that each cell in the diagnostic channel has equal probability to interact with the substrate and is independent of the presence or density of other cells. Likewise, each miaRBC has equal probability to be immobilized on the substrate. As the % infection increases, the total number of miaRBCs loaded into the diagnostic channel was also increased proportionally. Since each miaRBC has equal immobilization probability, the total number of captured miaRBCs under identical conditions should also hold a linear relationship to the total number of miaRBCs loaded. Thus, it follows that the relationship between % infection and miaRBCs capturing efficiency is linear. This leads to an important practical guideline that it is not necessary to capture all the miaRBCs loaded in the diagnostic channel to achieve an accurate diagnosis.

By controlling the concentration of blood sample and the length of the diagnostic channel, a linear relationship could be identified and be used as the reference to perform diagnosis on unknown blood samples. The clinical implication is that a small portion of captured miaRBCs could be used to determine the stage of infection without the need to identify miaRBCs from a large pool of non-infected aRBCs. Note also that the immobilization sensitivity and efficiency of non-infected aRBCs are below 0.05% independent of the infection stages. This implies a very low probability of immobilizing non-infected aRBCs on the substrate across all samples.

To verify that the capturing mechanism was influenced by the protrusions of the roughened substrates, identical experiments were conducted with HF treated glass substrates. The experimental results of using 2% HF treated substrate with ten-point-height of 3.1988 nm (average of ten measurements) did not show statistical improvement in immobilization sensitivity over untreated substrates with ten-point height of 2.0991 nm, showing variations between −5.5% to 5.5%. For reference, the depth of the furrow-like structures on miaRBCs were around 7.6 nm, more than twice the ten-point heights of both untreated and 2% HF treated glass substrates. However, significant increase in capturing sensitivity was observed by using 10% HF treated glass substrate, which had ten-point-height around 14.7238 nm, roughly twice the depth of the furrow-like structures. Generally, the protrusions of the roughened substrate or contact surface 20 should have nanometer-scale (e.g., nano-scale) feature sizes. For instance, heights between about 12 nm to about 16 nm would work well. The protrusions may also be characterized by ten-point-height measurements using, for instance, AFM measurements. Again, the range of ten-point-height measurements of these protrusions may fall within the range of about 12 nm to about 16 nm.

Figure 11:
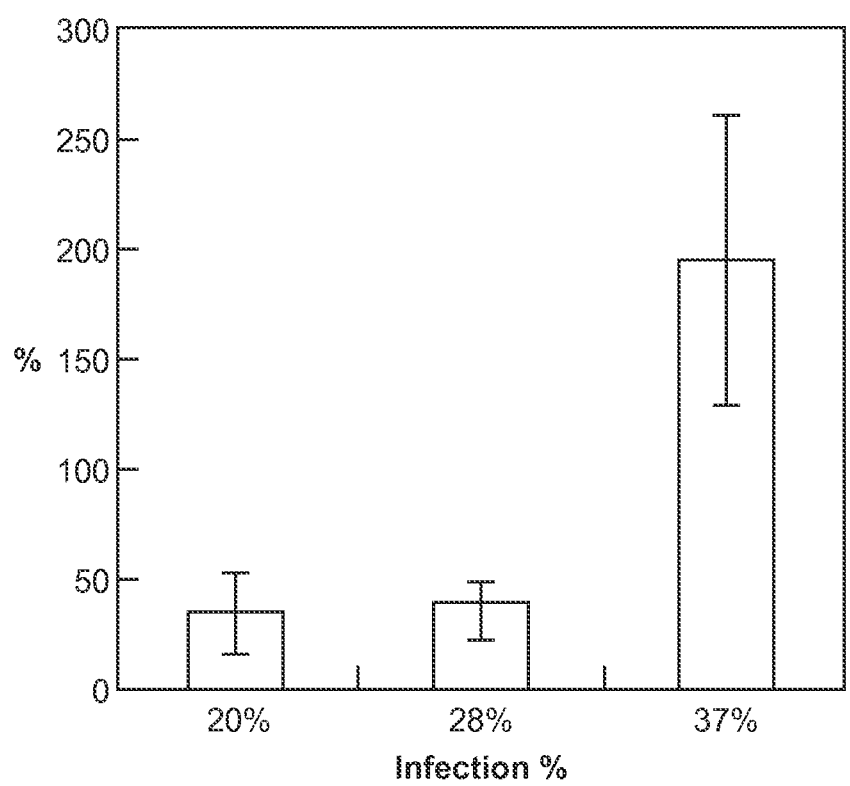
FIG. 11 illustrates a comparison chart of increased percentages of captured miaRBCs as a function of infection % for 10% HF treated glass substrates.

FIG. 11 compares the percentage of increased capturing efficiency of 10% HF treated glass substrate to untreated one for three different blood samples with different % infections. The shear rate was controlled to be around 2.14 $s^{-1}$. To accommodate the high % infection, the RBC concentrations were diluted to 5% v/v. The total captured miaRBCs increased by 34.4%, 37.9%, and 194.5% with 20%, 28% and 37% blood samples, respectively. This demonstrated that a roughened substrate with nano-scale protrusions twice the feature size of the surface lesions and furrow-like structures could provide a separation mechanism to capture miaRBCs.

While embodiments have been shown and described, various modifications may be made without departing from the scope of the inventive concepts disclosed herein. The invention(s), therefore, should not be limited, except to the following claims, and their equivalents.

What is claimed is:

1. A method of identifying infection by a malaria parasite comprising:
    obtaining a sample of whole blood comprising RBCs from a subject;
    flowing the sample through a microfluidic device having a channel comprising a contact surface at a flow rate sufficient to produce a shear rate between about 2.1 $sec^{-1}$ and 3.2 $sec^{-1}$, the contact surface being at least one of a hydrophilic contact surface and a roughened contact surface; and
    identifying the presence of infected RBCs, wherein RBC's infected with the malaria parasite are at least temporarily trapped on the contact surface and indicate infection and wherein RBC's not infected with the malaria parasite flow past the contact surface and are not trapped on the same.

2. The method of claim 1, wherein the contact surface comprises nano-scale features having an average feature size between about 12 to 16 nm.

3. The method of claim 1, wherein the contact surface has a root-mean-square surface roughness between about 0.1892 nm and 2.3286 nm.

4. The method of claim 1, wherein the contact surface is both hydrophilic and roughened.

5. The method of claim 1, wherein identifying the presence of infected RBCs comprises optical interrogation of the contact surface or a downstream region of the channel.

6. The method of claim 1, wherein the sample of whole blood is diluted prior flowing the sample through a microfluidic device.

7. A method of identifying infection by a malaria parasite comprising:
    obtaining a sample of whole blood comprising RBCs from a subject;
    flowing the sample at a first flow rate through a microfluidic device having a channel comprising a contact surface being at least one of a hydrophilic contact surface and a roughened contact surface, wherein infected RBCs are substantially trapped on the contact surface and wherein non-infected RBCs continue to flow through the microfluidic device;
    counting the number of non-infected RBCs in at least a portion of the sample flowing through the microfluidic device downstream of the contact surface;
    increasing the flow rate through the microfluidic device relative to the first flow rate so as to carry the infected RBCs trapped on the contact surface in fluid flow through the microfluidic device; and
    counting the number of infected RBCs in at least a portion of the sample flowing through the microfluidic device downstream of the contact surface.

8. The method of claim 7, wherein the first flow rate is sufficient to produce a shear rate between about 2.1 $sec^{-1}$ and 3.2 $sec^{-1}$.

9. The method of claim 7, wherein the contact surface comprises nano-scale features having an average feature size between about 12 to 16 nm.

10. The method of claim 7, wherein the contact surface has a root-mean-square surface roughness between about 0.1892 nm and 2.3286 nm.

11. The method of claim 7, wherein the counting comprises optically interrogating a region downstream of the contact surface.

12. The method of claim 11, wherein the downstream region is subject to sheath flow.

13. The method of claim 7, wherein the sample of whole blood is diluted prior flowing the sample through a microfluidic device.

* * * * *